United States Patent [19]
Turk et al.

[11] Patent Number: 5,958,409
[45] Date of Patent: Sep. 28, 1999

[54] METHOD FOR TREATING MULTIPLE SCLEROSIS

[75] Inventors: John Leslie Turk; David Baker; Marc Feldmann, all of London, United Kingdom

[73] Assignee: Kennedy Institute of Rheumatology, United Kingdom

[21] Appl. No.: 08/586,917

[22] PCT Filed: Jul. 30, 1993

[86] PCT No.: PCT/GB93/01614

§ 371 Date: Mar. 13, 1996

§ 102(e) Date: Mar. 13, 1996

[87] PCT Pub. No.: WO95/03827

PCT Pub. Date: Feb. 9, 1995

[51] Int. Cl.$^6$ .................. A61K 39/395; A61K 38/00
[52] U.S. Cl. .................. 424/141.1; 424/145.1; 424/156.1; 514/2; 530/350
[58] Field of Search ............ 424/130.1, 145.1, 424/141.1, 156.1; 514/2; 530/387.1, 388.1, 388.23, 350

[56] References Cited

U.S. PATENT DOCUMENTS

| 5,610,279 | 3/1997 | Brockhaus et al. | 530/387.3 |
| 5,656,272 | 8/1997 | Le et al. | 424/133.1 |

FOREIGN PATENT DOCUMENTS

| 0 512 528 A2 | 5/1992 | European Pat. Off. |
| 4 202 665 A1 | 1/1992 | Germany |
| WO 91/02078 | 2/1991 | WIPO |

OTHER PUBLICATIONS

Ruddle, N. H., et al., "An Antibody to Lymphotoxin and Tumor Necrosis Factor Prevents Transfer of Experimental Allergic Encaphalomyelitis", *J. Exp. Med.*, 172:1193–1200 (Oct. 1990).

Selmaj, K., et al., "Anti–Tumor Necrosis Factor Therapy Abrogates Autoimmune Demyelination", *Ann Neurol.*, 30(5):694–700 (1991).

Brennan, F. M. and Feldmann, M., "Cytokines in autoimmunity", *Current Opinion in Immunology*, 4(6):754–759 (Dec. 1992).

Gray, P.W., et al., "Cloning of Human Tumor Necrosis Factor (TNF) Receptor cDNA and Expression of Recombinant Soluble TNF–Binding Protein", *Proc. Natl. Acad. Sci. USA*, 87:7380–7384 (1990).

Brennan, F.M., et al., "Enhanced Expression of Tumor Necrosis Factor Receptor mRNA and Protein in Mononuclear Cells Isolated from Rheumatoid Arthritis Synovial Joints", *Eur. J. Immunol.*, 22:1907–1912 (1992).

Deleuran, B.W., et al., "Localization of Tumor Necrosis Factor Receptors in the Synovial Tissue and Cartilage–Pannus Junction in Patients with Rheumatoid Arthritis", *Arthritis and Rheumatism*, 35(10):1170–1178 (1992).

Williams, R.O., et al., "Anti–Tumor Necrosis Factor Ameliorates Joint Disease in Murine Collagen–Induced Arthritis", *Proc. Natl. Acad. Sci. USA*, 89:9784–9788 (1992).

Cope, A.P., et al., "Increased Levels of Soluble Tumor Necrosis Factor Receptors in the Sera and Synovial Fluid of Patients with Rheumatic Diseases", *Arthritis and Rheumatism*, 35(10):1160–1169 (1992).

Brennan, F.M., et al., "TNFα—A Pivotal Role in Rheumatoid Arthritis?", *British J. of Rheumatology*, 31:293–298 (1992).

Sharief, New England Journal of Medicine 325:467–472 (1991).

Teuscher, Clin. Immunol and Immunopathol. 54:442–453 (1990).

*Primary Examiner*—Toni R. Scheiner
*Assistant Examiner*—Nancy A. Johnson
*Attorney, Agent, or Firm*—Hamilton, Brook, Smith & Reynolds, P.C.

[57] ABSTRACT

A method for treating multiple sclerosis, through the administration of anti-tumour necrosis factor antibody, of soluble tumour necrosis factor receptor or of a compound capable of blocking tumour necrosis factor production, its effects and/or tumour necrosis factor receptor signal transduction, is disclosed. The method can be used to aid in therapy for humans and other mammals.

15 Claims, 8 Drawing Sheets

METHOD FOR TREATING MULTIPLE SCLEROSIS

This application is a 371 of PCT/GB93/01614, filed Jul. 30, 1993.

BACKGROUND

Multiple sclerosis (MS) is an autoimmune demyelinating disease of the central nervous system which usually presents in the form of recurrent attacks of focal or multifocal neurologic dysfunction. Attacks occur, remit, and recur, seemingly randomly over many years. Remission is often incomplete and as one attack follows another, a stepwise downward progression ensues with increasing permanent deficit.

Clinical disease is associated with blood-brain barrier dysfunction; infiltration of the central nervous system by mononuclear cells, mainly macrophages and T lymphocytes, and serum products; and demyelination (Harris J. O., et al., *Ann. Neurol.* 29:548 (1991); Kermonde A. G., et al., *Brain* 113:1477 (1990)).

Presently the nature of autoantigens responsible for multiple sclerosis is not known, nor is the action which triggers the autoimmune response. One popular theory involves the similarity of a viral protein to a self antigen, which results in autoreactive T cells or B cells recognizing a self antigen. Whereas B-lymphocytes produce antibodies, thymus-derived or "T-cells" are associated with cell-mediated immune functions. T-cells recognize antigens presented on the surface of cells and carry out their functions in association with "antigen-presenting" cells.

Currently no practical and efficacious treatments for multiple sclerosis exist. Thus, the development of a method for treating multiple sclerosis would be of immense benefit.

SUMMARY OF THE INVENTION

The present invention relates to a method of treating multiple sclerosis in a mammal. The invention is based on the discovery that tumour necrosis factor (TNF) has a role in the pathogenesis of multiple sclerosis and experimental allergic encephalomyelitis (EAE).

The method comprises administering to a mammal a therapeutically effective amount of an anti-tumour necrosis factor (anti-TNF) antibody which ameliorates the effects of multiple sclerosis. A therapeutically effective amount can be administered in the form of a single dose, or a series of doses separated by intervals of days, weeks or months.

Another method comprises administering to a mammal a therapeutically effective amount of a soluble TNF receptor which ameliorates the effects of multiple sclerosis. A therapeutically effective amount can be administered in the form of a single dose, or a series of doses separated by intervals of days, weeks or months.

Another method comprises administering to a mammal a therapeutically effective amount of a compound which is capable of blocking TNF production, its effects and/or tumour necrosis factor receptor signal transduction (anti-TNF compound).

The anti-TNF antibody, soluble TNF receptor or anti-TNF compound can be administered together with a pharmaceutically-acceptable vehicle. In a preferred embodiment administration of said antibody, soluble receptor or anti-TNF compound is by injection directly into the central nervous system of a human being. Injection directly into the central nervous system can be by injection directly into the lumbar cerebrospinal fluid (intrathecally). In another embodiment administration of said antibody, soluble receptor or anti-TNF compound is intravenously.

The present invention further relates to a pharmaceutical composition comprised of a pharmaceutically-acceptable carrier and a multiple sclerosis-therapeutically effective amount of anti-TNF antibody which ameliorates the effects of multiple sclerosis, soluble TNF receptor which ameliorates the effects of multiple sclerosis or anti-TNF compound.

The benefit of the method of therapy of the subject invention is that it provides an efficacious treatment for multiple sclerosis.

DETAILED DESCRIPTION OF THE INVENTION

Figure 1:
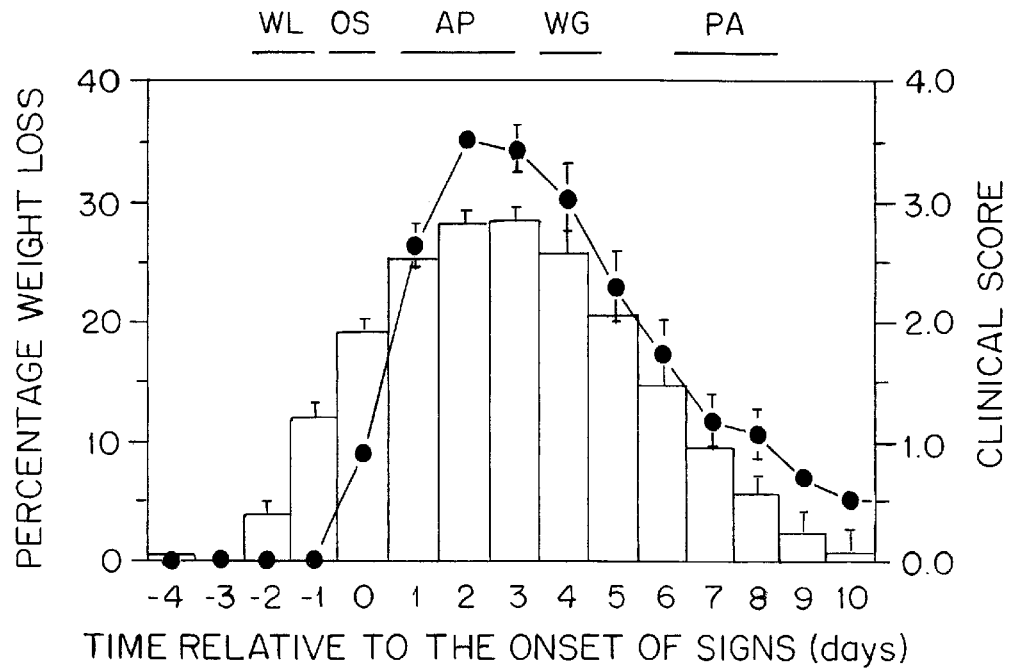
FIG. 1 is a histogram and a graph illustrating the kinetics of weight changes and clinical signs during acute phase chronic relapsing experimental allergic encephalomyelitis (CREAE) induced in Biozzi AB/H mice.

The present invention concerns the treatment of multiple sclerosis through the administration of anti-TNF antibody, of soluble tumour necrosis factor receptor (TNF-R) or of a compound capable of blocking tumour necrosis factor production, its effects and/or tumour necrosis factor receptor signal transduction (anti-TNF compound). Multiple sclerosis is an autoimmune disease of the central nervous system. The disease is associated with blood-brain barrier dysfunction, infiltration of the central nervous system by mononuclear cells (mainly macrophages and T lymphocytes, and serum products), and demyelination (Harris, J. O., et al., *Ann. Neurol.* 29:548 (1991); Kermonde, A. G., et al., *Brain* 113:1477 (1990)). Although CD4+ T lymphocytes are involved in the induction of the disease (Mokhtarian, F., et al., *Nature* 309:356–358 (1984); Waldor, M. K., et al., *Science* 227:415 (1985)), the effector mechanisms mediating pathogenesis of MS are unknown.

Tumour necrosis factor (TNF) has been implicated as an important effector molecule in the pathogenesis of various human diseases and animal models such as gram negative sepsis and rheumatoid arthritis (Tracey, K. J., et al., *Nature* 330:662 (1987); Brennan, F. M., et al., *Lancet* 2:244 (1989); Williams, R. O., et al., *Proc. Natl. Acad. Sci.* 89:9784 (1992)).

TNFα is a protein secreted primarily by monocytes and macrophages in response to endotoxin or other stimuli as a soluble homotrimer of 17 kD protein subunits (Smith, R. A., et al., *J. Biol. Chem.* 262:6951–6954 (1987)). A membrane-bound 26 kD precursor form of TNF has also been described (Kriegler, M., et al., *Cell* 53:45–53 (1988)). The expression of the gene encoding TNFα is not limited to cells of the monocyte/macrophage family: TNF is also produced by CD4+ and CD8+ peripheral blood T lymphocytes, and by various cultured T and B cell lines (Cuturi, M. C., et al., *J. Exp. Med.* 165:1581 (1987); Sung, S. -S. J., et al., *J. Exp. Med.* 168:1539 (1988); Turner, M., et al., *Eur. J. Immunol.* 17:1807–1814 (1987)).

The term antibody is intended to encompass both polyclonal and monoclonal antibodies. The term antibody is also intended to encompass mixtures of more than one antibody reactive with TNF (e.g., a cocktail of different types of monoclonal antibodies reactive with TNF). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to TNF.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies reactive with TNF can be produced using somatic cell hybridization techniques (Kohler and Milstein, *Nature* 256:495 (1975)) or other techniques. In a typical hybridization procedure, a crude or purified protein or peptide comprising at least a portion of TNF can be used as the immunogen. An animal is vaccinated with the immunogen to obtain anti-TNF antibody-producing spleen cells. The species of animal immunized will vary depending on the species of monoclonal antibody desired. The antibody producing cell is fused with an immortalizing cell (e.g., myeloma cell) to create a hybridoma capable of secreting anti-TNF antibodies. The unused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal with a crude or purified protein or peptide comprising at least a portion of TNF. The animal is maintained under conditions whereby antibodies reactive with TNF are produced. Blood is collected from the animal upon reaching a desired titre of antibodies. The serum containing the polyclonal antibodies (antisera) is separated from the other blood components. The polyclonal antibody-containing serum can optionally be further separated into fractions of particular types of antibodies (e.g., IgG, IgM).

Murine hybridomas which produce TNF specific monoclonal antibodies are formed by the fusion of mouse myeloma cells and spleen cells from mice immunized against a TNF positive T cells, purified TNF, or other biological preparations comprising TNF. To immunize the mice, a variety of different protocols may be followed. For example, mice may receive primary and boosting immunizations of TNF. The fusions are accomplished by standard procedures well known to those skilled in the field of immunology. Kohler and Milstein, *Nature,* 256:495 (1975) and Kennet, *Monoclonal Antibodies* (Kennet, et al., Eds. pp. 365, Plenum Press, N.Y., 1980).

The co-transfected resulting clones are then screened for production of antibody reactive with TNF or biological preparations comprising TNF. Those which secrete antibodies of the appropriate reactivity and specificity are cloned to yield a homogeneous cell line secreting anti-TNF antibody.

Human hybridomas which produce monoclonal anti-TNF antibodies are formed from the fusion of B cells from an individual producing anti-TNF antibodies and a human B lymphoblastoid cell line. Alternatively, the fusion partner for the myeloma cell may be a peripheral blood anti-TNF producing lymphocyte. The fusion and screening techniques are essentially the same as those used in the production and selection of murine anti-TNF generating hybridomas.

Also mouse and human hybridomas which produce human anti-TNF antibody may be formed from the fusion of a human antibody producing cell and a murine plasmacytoma cell or a cell which itself is a hybrid having the appropriate properties such as the ability to fuse with human lymphocytes at high frequency; support the synthesis and secretion of high levels of antibody; support the secretion of antibody for prolonged periods of time in culture.

Another way of forming the anti-TNF producing cell line is by transformation of antibody producing cells. For example, an anti-TNF producing B lymphocyte may be infected and transformed with a virus such as Epstein-Barr virus in the case of B lymphocytes to yield an immortal anti-TNF producing cell. See e.g., Kozbor and Roder, *Immunology Today,* 4(3):72 (1983). Alternatively the B lymphocyte may be transformed by a transforming gene or transforming gene product.

The TNF specific monoclonal antibodies are produced in large quantities by injecting anti-TNF antibody producing hybridomas into the peritoneal cavity of mice or other appropriate animal hosts and, after appropriate time, harvesting the resulting ascitic fluid which contains a high titre of antibody and isolating the monoclonal anti-TNF antibody therefrom. Allogeneic or xenogeneic hybridomas should be injected into immunosuppressed, irradiated or athymic nude mice. Alternatively, the antibodies may be produced by culturing anti-TNF producing cells in vitro and isolating secreted monoclonal anti-TNF antibodies from the cell culture medium.

Chimeric anti-TNF antibodies are produced by cloning DNA segments encoding the heavy and light chain variable regions of a non-human antibody specific for TNF and joining these DNA segments to DNA segments encoding human heavy and light chain constant regions to produce chimeric immunoglobulin encoding genes. The fused gene constructs coding for the light and heavy chains are assembled in or inserted into expression vectors. The genes are co-transfected into a lymphoid recipient cell (e.g., a myeloma cell) where the immunoglobulin protein can be synthesized, assembled and secreted. The transfected recipient cells are cultured and the expressed immunoglobulins are collected.

A more detailed description of anti-TNF antibodies and their use in treatment of disease is contained in the following references, the teachings of which are incorporated by reference: U.S. application Ser. No. 07/943,852, filed Sep. 11, 1992; Rubin, et al., EPO Patent Publication 0218868, Apr. 22, 1987; Yone, et al., EPO Patent Publication 0288088, Oct. 26, 1988; Liang, C. -M., et al., *Biochem. Biophys. Res. Comm.* 137:847 (1986); Meager, A., et al., *Hybridoma* 6:305 (1987); Fendly, et al., *Hybridoma* 6:359 (1987); Bringman, T. S., et al., *Hybridoma* 6:489 (1987); Hirai, M., et al., *J. Immunol. Meth.* 96:57 (1987); Moller, A., et al., *Cytokine* 2:162 (1990); Mathison, J. C., et al., *J. Clin. Invest.* 81:1925 (1988); Beutler, B., et al., *Science* 229:869 (1985); Tracey, K. J., et al., *Nature* 330:662 (1987); Shimamoto, Y., et al., *Immunol. Lett.* 17:311 (1988); Silva, A. T., et al., *J. Infect. Dis.* 162:421 (1990); Opal, S. M., et al., *J. Infect. Dis.* 161:1148 (1990); Hinshaw, L. B., et al., *Circ. Shock* 30:279 (1990).

Particular preferred antibodies are TNF-specific antibodies with a high binding affinity, i.e., with an association constant K of at least $10^8$ liters per mole. The association constant K can be determined by equilibrium dialysis as described in Kuby, J., *Immunology*, W.H. Freeman & Co., New York, 1992, pp. 122–124.

A more detailed description of antibody affinity and he association constant K is contained in the following references, the teachings of which are incorporated by reference: Kuby, J., *Immunology*, W.H. Freeman & Co., New York, 1992, pp. 122–124; Hood, L. E., et al., *Immunology*, Second Edition, The Benjamin/Cummings Publishing Co., Menlo Park, Calif., 1984, pp. 58–60; Abbas, A. K., et al., *Cellular and Molecular Immunology*, W.B. Saunders Co., Philadelphia, 1991, pp. 53–54.

The term soluble receptor is intended to encompass cloned soluble whole receptors, biologically functional fragments thereof, and cloned soluble chimeric receptors. The term soluble receptor is further intended to include all cloned soluble molecules which neutralize tumour necrosis factor (i.e, bind to TNF) or which inhibit TNF biological activity. Biologically functional receptor fragments which can be used are those fragments sufficient for binding of the tumour necrosis factor or those fragments capable of inhibiting TNF biological activity.

Cloned soluble chimeric receptors include those molecules capable of binding TNF which are made by fusion of a portion of a TNF receptor to at least one immunoglobulin heavy or light chain. The portion of the TNF receptor present in the cloned chimeric receptor consists of at least a portion of the extracellular region of the TNF receptor. Other types of fusions which result in molecules that are capable of binding TNF are also included.

The chimeric receptors can comprise portions derived from two different species (e.g., extracellular domain of human TNF receptor and $C_H2$ through $C_H3$ domains of murine IgG1 heavy chain). The portions derived from two different species can be joined together chemically by conventional techniques or can be prepared as single contiguous proteins using genetic engineering techniques as described in Peppel, K., et al., *J. Exp. Med.* 174:1483–1489 (1991). DNA encoding both portions of the chimeric receptor can be expressed as contiguous chimeric receptor proteins.

The chimeric receptors can comprise two portions derived from the same species (e.g., extracellular domain of human TNF receptor and constant domains of human IgG heavy chain). The two portions can be joined together chemically by conventional techniques or can be prepared as single contiguous proteins using genetic engineering techniques as described in Lesslauer, W., et al., *Eur. J. Immunol.* 21:2883–2886 (1991), and Ashkenazi, A., et al., *Proc. Natl. Acad. Sci. USA* 88:10535–10539 (1991). DNA encoding both portions of the chimeric receptor can be expressed as contiguous chimeric receptor proteins.

Other chimeric TNF receptor compositions are possible and can be employed in the subject invention. (See e.g., Scallon, B., et al., U.S. application Ser. No. 08/010,406, filed Jan. 29, 1993). A more detailed description of chimeric TNF receptors and their ability to bind TNF is contained in the following references, the teachings of which are incorporated by reference: Scallon, B., et al., U.S. application Ser. No. 08/010,406, filed Jan. 29, 1993; Peppel, K., et al., *J. Exp. Med.* 174:1483 (1991); Lesslauer, W., et al., *Eur. J. Immunol.* 21:2883 (1991); Ashkenazi, A., et al., *Proc. Natl. Acad. Sci. USA* 88:10535 (1991).

Compounds and ligands capable of blocking TNF production, its effects and/or tumour necrosis factor receptor signal transduction but which are not receptors can also be employed in the subject invention. Such compounds include, but are not limited to, peptides, anti-TNF drugs and anti-TNF signal transduction compounds.

Anti-TNF antibodies, soluble TNF receptors or anti-TNF compounds are useful if, upon administration to the host in an effective amount, they ameliorate the clinical symptoms or causes of multiple sclerosis. The symptoms or causes are ameliorated if they are significantly reduced or eliminated.

It is desirable to administer the anti-TNF antibodies, soluble TNF receptors, and anti-TNF compounds employed in the subject invention directly to the central nervous system. However, the existence of the blood-brain barrier limits the free passage of many types of molecules from the blood to cells of the central nervous system (e.g., potentially useful and therapeutic agents such as anti-TNF antibodies and soluble TNF receptors). During the active phase of inflammatory diseases such as MS and EAE, blood brain leakage is known to occur and will permit entry of anti-TNF antibody, soluble TNF receptors or anti-TNF compounds to the central nervous system. Nevertheless, there are several techniques that either physically break through the blood-brain barrier or circumvent it to deliver therapeutic agents. Examples of these techniques include intrathecal injections, surgical implants, and osmotic techniques. In addition, the permeability of the blood-brain barrier to anti-TNF antibodies, soluble TNF receptors, and anti-TNF compounds can be increased by administering a bradykinin agonist of blood-brain permeability (e.g., N-acetyl [Phe$^8$ (CH$_2$-NH)Arg$^9$] bradykinin). A more detailed description of these techniques that either physically break through the blood-brain barrier or circumvent it are contained in Malfroy-Camine, U.S. Pat. No. 5,112,596, May 12, 1992, the teachings of which are incorporated by reference.

A preferred embodiment for the administration of the antibodies, soluble receptors and anti-TNF compounds is by intrathecal injection, i.e., directly into the cerebrospinal fluid by puncturing the membranes surrounding the central nervous system. Puncturing of the membranes surrounding the central nervous system is usually by lumbar puncture. Sustained dosages of agents directly into the cerebrospinal fluid can be attained by the use of infusion pumps that are implanted surgically.

Another embodiment for the administration of anti-TNF antibodies, soluble TNF receptors, and anti-TNF compounds is by injection directly into the lumbar cerebrospinal fluid (intrathecally) or by injection intravenously. Other methods and modes of administration can also be employed.

The pharmaceutically-acceptable form in which the anti-TNF antibody, soluble TNF receptor, or anti-TNF compound is administered will depend, at least in part, on the route by which it is administered. For example, in the case of administration by injection, the anti-TNF antibody, soluble TNF receptor, or anti-TNF compound can be formulated with conventional pharmaceutically-acceptable vehicles into pharmaceutical compositions in the usual way for that route of administration. Such vehicles are inherently non-toxic and nontherapeutic.

A therapeutically effective amount of anti-TNF antibody, soluble TNF receptor, or anti-TNF compound is that amount necessary to significantly reduce or eliminate symptoms associated with multiple sclerosis. An efficacious amount of anti-TNF antibody for mice is in the range of 150 $\mu$g –1 mg/injection. Therefore, a reasonable and preferred therapeutically effective amount of anti-TNF antibody for humans is in the range of 0.1–50 mg/kg/dose. Similarly, a preferred therapeutically effective amount of soluble TNF receptor for mice is in the range of 15–150 $\mu$g/injection. Therefore, a reasonable and preferred therapeutically effective amount of soluble TNF receptor for humans is in the range of 0.1–10 mg/kg/dose. The therapeutically effective amount will be determined on an individual basis and will be based, at least in part, on consideration of the individual's size, the severity of symptoms to be treated, the result sought, etc. Thus, the therapeutically effective amount can be determined by one of ordinary skill in the art employing such factors and using no more than routine experimentation.

The therapeutically effective amount can be administered in the form of a single dose, or a series of doses separated by intervals of days, weeks or months. Once the therapeutically effective amount has been administered, a maintenance amount of anti-TNF antibody, of soluble TNF receptor, or of anti-TNF compound can be administered. A maintenance amount is the amount of anti-TNF antibody, soluble TNF receptor, or anti-TNF compound necessary to maintain the reduction or elimination of symptoms achieved by the therapeutically effective dose. The maintenance amount can be administered in the form of a single dose, or a series of doses separated by intervals of days, weeks or months. Like the therapeutically effective amount, the maintenance amount will be determined on an individual basis.

Other anti-inflammatory or anti-immune drugs, such as methotrexate or cyclosporin A, or antibodies, such as anti-CD4 antibodies, can be administered in conjunction with the anti-TNF antibody, the soluble TNF receptor, or the anti-TNF compound. (See e.g., Feldmann, M., et al., U.S. application Ser. No. 07/958,248, filed Oct. 8, 1992).

The method of the present invention can be used to treat multiple sclerosis or any related disease in any mammal. In a preferred embodiment, the method is used to treat multiple sclerosis in human beings.

Described herein is work which illustrates the effect of anti-TNF antibody and soluble TNF-R IgG fusion protein in EAE, the results of which indicate that blocking TNF biological activity or other TNF effects, or blocking TNF receptor signal transduction is useful in treating MS.

The experiments described herein utilizes EAE as an experimental model of the human demyelinating disease multiple sclerosis. Chronic relapsing EAE is an autoimmune demyelinating disease of the central nervous system used as an experimental model of MS.

This mouse model of induced EAE has similarities to human MS in its clinical signs. In both EAE and MS, clinical disease is associated with blood-brain barrier (BBB) dysfunction, infiltration of central nervous system by mononuclear cells (mainly macrophages and T lymphocytes, and serum products), and demyelination (Baker, D., et al., *J. Neuroimmunol.* 28:261 (1990); Butter, C., et al., *J. Neurol. Sci.* 104:9 (1991); Harris J. O., et al., *Ann. Neurol.* 29:548 (1991); Kermonde A. G., et al., *Brain* 113:1477 (1990)). Thus, the mouse model serves as a good approximation to human disease.

To facilitate the determination of whether TNF is important in the pathogenesis of neuroimmunological diseases such as EAE and MS, a TNF-specific monoclonal antibody (TN3.19.12) was administered as described in Examples 5, 6 and 7 during actively-induced EAE (Example 1), shortly before (1–2 days) pre-clinical weight loss, when BBB dysfunction and infiltration of the central nervous system became apparent (Example 2) (Butter, C., et al., *J. Neurol. Sci.* 104:9 (1991)), and during active clinical disease when neurological signs were manifested (Example 1), and a soluble human TNF receptor (human p55 TNF-R) was administered as described in Examples 8 and 9 during actively-induced EAE, shortly following the onset of clinical signs. As described in Examples 5, 6, 7, 8 and 9, TNF immunotherapy was found to inhibit the progression of chronic relapsing EAE, and thus has implications for the therapeutic strategies in the human disease multiple sclerosis.

As described in Example 2, the disease episodes of chronic relapsing EAE are associated with BBB dysfunction (FIG. 2) and marked cellular infiltration of the central nervous system (Baker, D., et al., *J. Neuroimmunol.* 28:261 (1990); Butter, C., et al., *J. Neurol. Sci.* 104:9 (1991)). As described in Examples 1, 2 and 3, these parameters which are modulated by anti-TNF antibody (Table 2), correlated with progressive weight loss which occurs shortly before the detection of clinical neurological deficit (FIG. 1).

The ability of TNF to augment clinical disease (Kuroda, Y., et al., *J. Neuroimmunol.* 34:159–164 (1991)) and induce the production of other proinflammatory cytokines (Beutler, B., et al., *Science* 229:869 (1985); Brennan, F. M., et al., *Lancet* 2:244 (1989)), and the inhibition of EAE following TNF-neutralization as described herein, implicates an important proinflammatory role for TNF in the pathogenesis of EAE. As described in Examples 5, 6 and 7, clinical EAE developed following the cessation of antibody therapy, indicating that TNF immunotherapy is not exerting an effect through generalized immunosuppression.

As described in Example 4, in contrast to the immunosuppressive action of CD4-specific monoclonal antibody on EAE and T cell proliferation, inhibition of TNF activity exhibited minimal effects on T proliferative responses (FIG. 5), indicating that TNF-directed immunotherapy targets effector cell function rather than the induction of disease and consistent with the inability of in vitro treatment of encephalitogenic cells to inhibit adoptive transfer of disease (Selmaj, K., et al.,*Ann. Neurol.* 30:694 (1991)). Therefore the relative timing of antibody administration is important for an inhibitory effect to be observed. For example, in contrast to the inhibitory effect of multiple doses observed when treatment was administered during the anticipated development of disease (Table 1), similar treatment (3×250 $\mu$g TN3.19.12 injected intraperitoneally) terminated prior to development of anticipated clinical disease failed to prevent the development of clinical EAE (8 of 8 affected with a mean group score of 3.3±0.5).

As described in Examples 5, 6 and 7, although systemic administration of neutralizing TNF antibodies inhibited EAE (FIGS. 4A–4B, 7 and 8A–8C), significantly increased benefit was observed when TNF was administered directly into the central nervous system (FIGS. 7 and 8A–8C), indicating that the majority of TNF activity is generated within the central nervous system. Antibodies have a limited potential to cross the intact blood brain barrier (Hafler, D. A., et al., *Ann. Neurol.* 21:89 (1987)). However, if TNF-specific monoclonal antibody is administered systemically to multiple sclerosis patients, increased targeting of antibody into the central nervous system would occur when blood-brain barrier dysfunction is present, which frequently occurs in clinically silent MS (Harris, J. O., et al., *Ann. Neurol.* 29:548 (1991); Kermonde, A. G., et al., *Brain* 113:1477 (1990)), as well as during clinical episodes.

The Examples described herein demonstrate the important role of TNF in the demyelinating disease EAE, an experimental model of MS, thereby indicating that TNF is a suitable target for immune intervention and indicating a method for treating multiple sclerosis. Further, the work described herein indicate the advantages of administering TNF antibodies, soluble TNF receptors or anti-TNF compounds directly into the central nervous system.

In addition, unlike previous studies using anti-TNF in EAE where the effect on EAE was limited only if the antibody was given before the onset of clinical manifestations, i.e., prophylactically (Selmaj, K., et al., *Ann. Neurol.* 30:694 (1991); Ruddle, N., *J. Exp. Med.* 172:1193 (1990)), the work described herein demonstrate therapy after the onset of clinical manifestations, a situation which is relevant to treating multiple sclerosis in human beings.

The present invention is further illustrated by the following Examples, which are not to be limiting in any way.

EXAMPLE 1

Induction of Experimental Allergic Encephalomyelitis

Inbred Biozzi AB/H (H-$2^{dq1}$) mice were injected with 1 mg of spinal cord homogenate (SCH) emulsified with Freund's incomplete adjuvant supplemented with 60 µg mycobacteria (*Mycobacteria tuberculosis* H37Ra and *M. butyricum* in an 8 to 1 ratio) on days 0 and 7 as described previously (Baker, D., et al., *J. Neuroimmunol.* 28:261 (1990)). From day 11 (D11) post-inoculation (p.i.) onwards the mice were weighed and checked for clinical signs (FIG. 1). These signs were graded as follows: 0=normal, 1=totally limp tail, 2=impaired righting reflex, 3=partial hindlimb paralysis and 4=complete hindlimb paralysis. Neurological signs of lower severity than typically observed were scored 0.5 lower than the grade indicated (Baker, D., et al., *J. Neuroimmunol.* 28:261 (1990)).

Clinical phases of acute EAE have been described previously (Allen, S. J., et al., *Cell Immunol.* 146:335 (1993)). Briefly weight loss (WL), initially of more than 1.5 grammes/day, occurred generally on days 13–15 p.i. This was followed by the onset of signs (OS), manifested by a flaccid tail, on days 15–17 p.i. and by days 17–19 p.i. animals were experiencing acute phase paralysis (AP), grade 3–4. Paralysed animals (grade 3–4) eventually exhibited a weight gain (WG) and clinical signs began to abate during the post-acute (PA) period with animals showing grade 2–1 disease, generally by days 21–23 p.i. (FIG. 1). Typically by day 24 p.i. animals have entered a period of clinical and histological remission (Baker, D., et al., *J. Neuroimmunol.* 28:261 (1990)) when the central nervous system is again relatively impermeable to the entry of lymphocytes and serum proteins (Butter, C., et al., *J. Neurol. Sci.* 104:9 (1991)).

FIG. 1 illustrates the kinetics of weight changes and clinical signs during acute phase chronic relapsing experimental allergic encephalomyelitis (CREAE) induced in Biozzi AB/H mice. The data depicted shows that active clinical disease correlates with progressive weight changes. Each bar on the histogram represents the mean percentage loss of body weight, relative to that expressed 3 days prior to the onset of clinical disease and each circle on the graph represents the mean clinical score relative to the day of onset of clinical disease on day 0. The data represents the mean ±SEM of 13 individual mice. The relative times of the different disease phases are indicated. Abbreviations correspond to the following phases: WL=weight loss; OS=onset of signs; AP=acute paralysis; WG=weight gain; and PA=post-acute.

EXAMPLE 2

Blood-brain Barrier Function

At various time points following EAE induction (Example 1), mice were injected intravenously with 2.5× $10^7$ $^{51}$Cr-labelled lymph node cells and 5 µCi $^{125}$I-albumin as described previously (Butter, C., et al., *J. Neurol. Sci.* 104:9 (1991)). Eighteen hours later anesthetized animals were perfused with RPMI-1640 medium, via the left ventricle following the removal of a 20 µl blood sample. Brains and spinal cords of 4–14 animals per group were collected and estimations of the radioisotope concentrations were performed with a γ-spectrometer. The results are expressed as the number of donor cells per gramme of target tissue and extravascular blood equivalents (EVBE), where 100 EVBE are equivalent to the $^{125}$I-albumin plasma protein concentration in blood at the time of sampling, as described previously (Butter, C., et al., *J. Neurol. Sci.* 104:9 (1991)).

Figure 2:
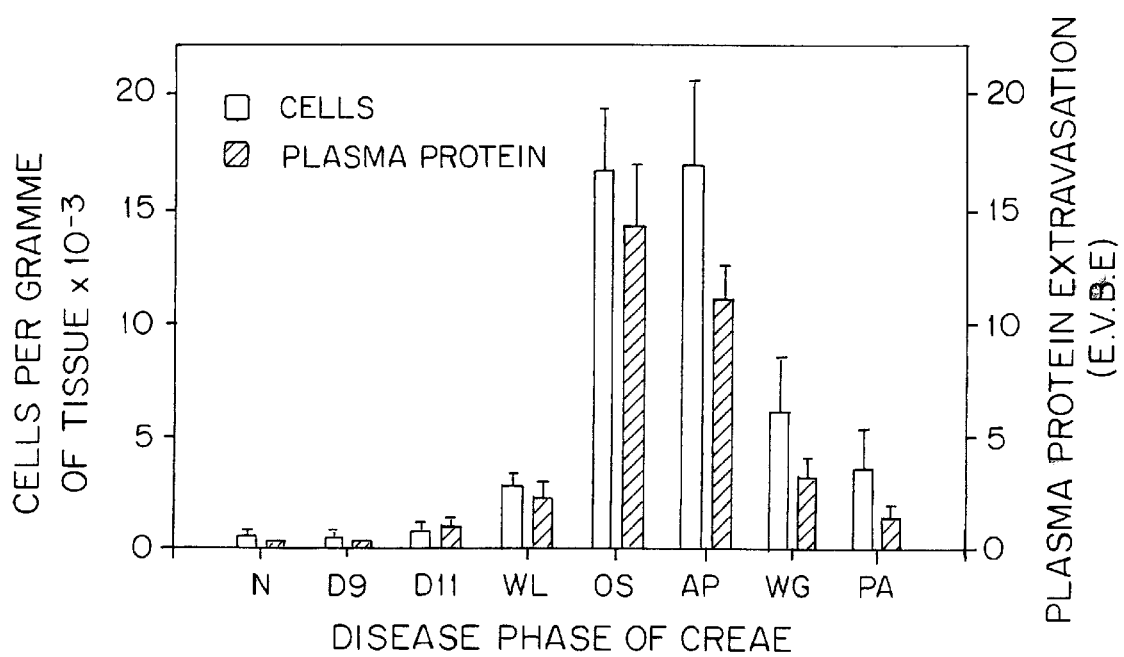
FIG. 2 is a histogram illustrating blood-brain barrier permeability to cells and protein during acute phase CREAE.

FIG. 2 illustrates the blood-brain barrier permeability during acute phase chronic relapsing EAE. Open bars represent the permeability of the spinal cord to cells and hatched bars represent the permeability of the spinal cord to plasma protein. The results represent the mean±SEM of between 4–14 animals per group.

In normal (N) animals and up to day 11 post-inoculation following the induction of EAE, the central nervous system was relatively impermeable to trafficking of lymph node cells and plasma protein (FIG. 2). Plasma protein extravasation and cellular traffic both correlated with the development of clinical disease.

BBB breakdown was first detectable in the brain (data not shown), which is relatively uninvolved during EAE in AB/H mice (Baker, D., et al., *J. Neuroimmunol.* 28:261 (1990); (Butter, C., et al., *J. Neurol. Sci.* 104:9 (1991)), and the spinal cord (FIG. 2) when animals experienced weight loss. Blood-brain barrier permeability dramatically increased as clinical signs (OS and AP) developed and weight loss (a total of 25–35% of the body weight compared with day 12) progressed. Once weight gain became apparent in paralysed animals, BBB permeability markedly declined. Clinical signs abated during the post-acute phase and, as previously reported (Butter, C., et al., *J. Neurol. Sci.* 104:9 (1991)), the integrity of BBB was restored in remission animals. The results indicate that BBB dysfunction correlates with progressive weight changes.

EXAMPLE 3

Detection of Tumour Necrosis Factor Activity

Tissue Fluids

Serum samples were prepared following exsanguination into the thoracic cavity, of terminally anesthetized animals during various phases of EAE. Cerebrospinal fluid (CSF) samples (1–3 μl/animal) were withdrawn from *foramen maanum* into a haematocrit tube. Following centrifugation to remove cells, these samples were stored at −20° C. prior to assay. Tumour necrosis activity was assessed using either the TNF-sensitive mouse fibroblast cell line L929, as described previously (Beutler B., *Science* 229:869 (1985)), or 1:2 dilutions of serum, and 1:50 dilutions of CSF were assayed using the Factor-Test mouse TNFα ELISA kit (Genzyme, UK), according to the manufacturer's instructions. The ELISA assay could detect 50 pg/ml –3.2 ng/ml of TNFα.

Tissue sections

Acetone-fixed cryostat sections of cervical spinal cord were stained within 1 week of preparation by an indirect immunoperoxidase technique essentially as described previously (Baker, D., et al., *J. Neuroimmunol.* 28:261 (1990)). Briefly, endogenous peroxidase activity was blocked. Sections were incubated with 5% normal mouse serum (NMS) for 30 minutes followed by a 1 hour incubation with primary monoclonal antibody reactive with mouse TNFα/β, for example with TN3.19.12 monoclonal antibody, a hamster immunoglobulin G1 (IgG1) monoclonal antibody which neutralizes mouse TNFα and TNFβ (Sheehan, K. C. F., et al., *J.Immunol.* 142:3884 (1989)) (supplied by Dr. R. Schreiber, Washington University Medical School, St. Louis, USA in conjunction with Celltech, Slough, UK), or with primary monoclonal antibody reactive with rat anti-mouse TNFα, for example with MP6-XT3 [HB10649] or MX6-XT22 [HB10697] both rat IgG1 monoclonal antibodies produced by hybridoma cell cultures (obtained from ATCC, courtesy of Dr. J. Abrams, DNAX, USA).

The primary monoclonal antibodies were detected by sequential 30 minute incubations with biotinylated goat anti-hamster immunoglobulin or rabbit anti-rat immunoglobulin, avidin:biotin peroxidase complex and peroxidase conjugated rabbit anti-goat immunoglobulin or swine anti-rabbit immunoglobulin, respectively. The reaction product was developed using the chromogen diaminobenzidine. Sections were counterstained with haematoxylin. In some instances the primary monoclonal antibody was diluted with excess recombinant mouse TNFα (200–500 μg/ml) prior to use for immunocytochemistry. This process failed to inhibit the staining of sections with a CD8-specific monoclonal antibody.

For double labelling, sections were incubated with rat anti-mouse TNFα, rabbit anti-rat immunoglobulin, and a 1:100 dilution (in phosphate buffered saline (PBS) containing 5% NMS) of swine anti-rabbit immunoglobulin which was conjugated with either tetra rhodamine isothiocyanate (TRITC) or fluorescein isothiocyanate (FITC). Rabbit anti-Factor VIII-related antigen and rabbit anti-glial fibrillary acidic protein (GFAP) were conjugated with FITC and extensively dialyzed. Double immunofluorescence staining was then performed by incubating these sections with 1:50–1:100 dilutions (in 5% NMS) of either: FITC conjugated anti-Factor VIII, anti-GFAP, H-2A specific mouse monoclonal antibody, or phycoerythrin conjugated rat immunoglobulin monoclonal antibody specific for B cell restricted B220, CD4 or CD8 antigens for 30 minutes. Sections were observed by fluorescence microscopy.

Detection of TNF

The data shown in FIG. 2 suggested that blood brain barrier dysfunction correlated with the weight loss of the animals. However, initial examination of sera from WL and AP animals, with the L929 cell line, failed to demonstrate the presence of biologically active TNF. Furthermore analysis of 5 individual samples of sera from WL, OS, AP and PA animals and CSF samples from 5 paralysed (AP) animals indicated that the level of TNF present was below the sensitivity of the TNFα ELISA assay used, indicating that at least in the serum samples, there was less than 100 pg/ml of TNFα. However, it was possible to detect TNF within the central nervous system of chronic relapsing EAE animals using immunocytochemistry.

Although some TNF-specific monoclonal antibodies (MX6-XT22 [HB10649] and TN3.19.12) failed to produce satisfactory staining throughout a range of doses, suggesting that the tissue area which is recognized by these antibodies may be denatured, the TNF-specific monoclonal antibody MP6-XT3 (20 μl of 4–8 μg/ml) revealed staining which was blocked by co-incubation of the monoclonal antibody with recombinant mouse TNFα. Immunostaining demonstrated TNFα activity within lesions present in the cervical spinal cord of paralysed animals and on some lesions of post-acute animals although the intensity of staining appeared reduced compared with that observed in paralysed (AP) animals.

TNFα was present in mononuclear cells within perivascular lesions and was often concentrated at the parenchyma/lesion edge where positive cells appeared macrophage/glial-like. Although some positive cells also appeared to have the morphology of astrocytes, the resolution of the immunoperoxidase stained tissue precluded accurate identification of the cells expressing TNF.

Immunofluorescence detection of TNFα on $CD4^+$ T lymphocytes, astrocytes and macrophages in spinal cord lesions during chronic relapsing EAE shows that this distribution is similar to that observed in multiple sclerosis lesions (Hoffman, F. M., et al., *J. Exp. Med.* 170:607 (1989); Selmaj, K., et al., *J. Clin. Invest.* 87:949 (1991)).

Tumour necrosis factor (TNFα) was detected by either FITC or TRITC conjugated antibody in the spinal cord lesions of paralysed EAE animals. Sections were incubated with either a phycoerythrin conjugated CD4-specific monoclonal antibody or FITC conjugated Factor VIII related-antigen, GFAP or H-2A-specific antibodies.

During the acute phase of chronic relapsing EAE both B cells and $CD8^+$ T lymphocytes formed a minor component of the cellular infiltrate and B cells generally failed to show any evidence of TNFα activity by double immunofluorescence staining. Occasionally some $CD4^+$ T lymphocytes within perivascular lesions expressed TNFα.

Although TNF activity was detected in close proximity to blood vessels, staining typically failed to co-localize with endothelial cells stained by anti-Factor VIII-related antigen.

While some $GFAP^+$ astrocytes expressed TNFα, particularly in areas adjacent to perivascular lesions, the majority of detectable TNFα activity co-localized with macrophage/microglia cells expressing MHC class II antigens.

EXAMPLE 4

Oxazolone Proliferative Assay

Animals were painted on one ear with 25 μl of 2.5% oxazolone (OX, Sigma, Poole, UK) dissolved in 4:1 acetone:olive oil (AOO) on day 0 (O'Neill, J. K., et al., *J. Neuroimmunol.* 35:53 (1992)). On day 2 the animals (3–4 per group) were injected intraperitoneally (i.p.) with 0.1 ml of TNF- or CD4-specific monoclonal antibodies diluted in PBS (500 μg TN3.19.12, a TNF-specific monoclonal antibody, or approximately 250 μg YTS 177.9, a rat IgG2a monoclonal antibody which is a non-depleting mouse CD4-specific antibody (Qin, S., et al., *Eur. J. Immunol.* 20:2737 (1990)) produced in ascites fluid.

Three days after the topical application of oxazolone, the draining auricular lymph nodes from each 3–4 animals per group were removed and pooled, and the induced proliferative response assessed as previously described (O'Neill, J. K., et al., *J. Neuroimmunol.* 35:53 (1992)). Briefly, $5\times10^5$ cells/well were cultured overnight (in the absence of exogenous oxazolone) at 37° C. in a humidified atmosphere of 5% $CO_2$ in air with 2 μci of [methyl-$^3$H] thymidine (specific activity 2 Ci/mmol). Cultures were harvested and [$^3$H] thymidine incorporation was determined by β-scintillation counting.

Figure 5A:
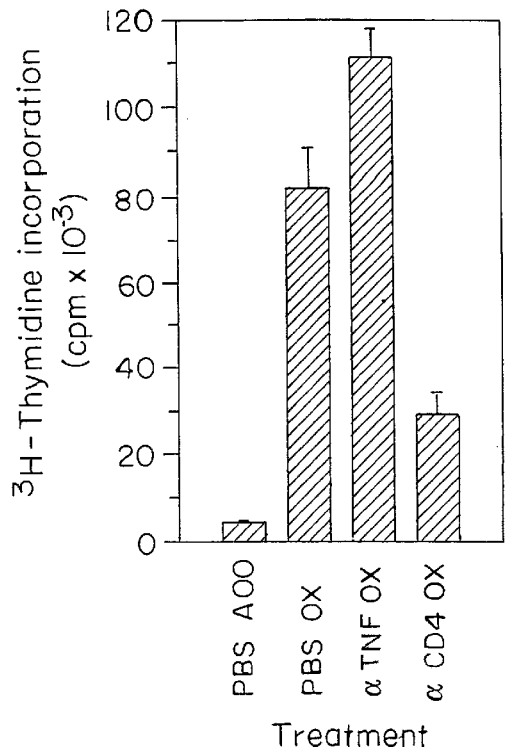
FIG. 5 is a pair of graphs showing that anti-TNF, unlike anti-CD4, is not immunosuppressive and does not diminish the proliferative response to the contact sensitizer oxazolone.
Figure 5B:
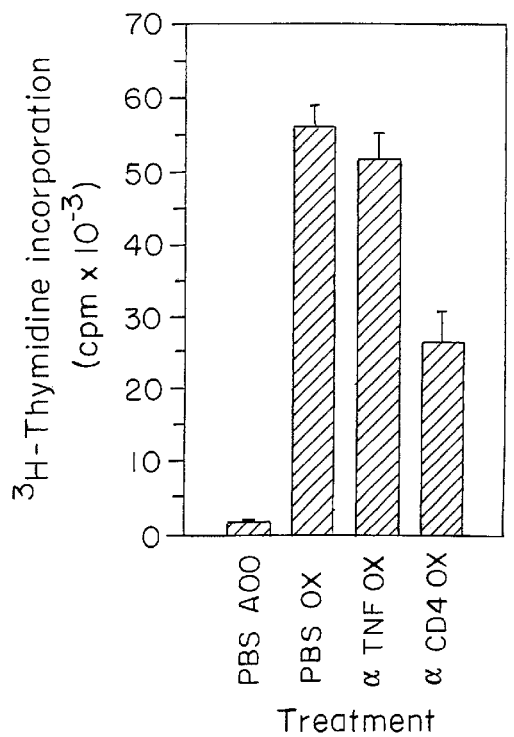

FIG. 5 shows the results of the effect of TNF immunotherapy on an in vivo induced T cell proliferative response from two individual experiments. The data depicted shows that in contrast to the immunosuppressive action of the CD4-specific antibody, the anti-TNF antibody did not inhibit T cell proliferative function under the conditions tested, indicating that these immunomodulatory compounds operate via different mechanisms. The results represent the mean ±SD of a minimum of 5 replicate wells.

EXAMPLE 5

Systemic anti-TNF Immunotherapy

To elucidate the potential role of TNF in a chronic relapsing EAE model, animals were injected with TN3.19.12, an anti-TNF monoclonal antibody. TN3.19.12 monoclonal antibody (supplied by Dr. R. Schreiber, Washington University Medical School, St. Louis, USA) has a serum half-life of approximately 7 days (Sheehan K. C. F., et al.,*J. Immunol.* 142:3884 (1989)) and a single injection of 300 μg of TN3.19.12 monoclonal antibody has been reported to inhibit the development of relapsing EAE induced by cell-transfer (Ruddle N. H., et al., *J. Exp. Med.* 172:1193 (1990)). However, a single intraperitoneal injection of 250 μg of TN3.19.12 monoclonal antibody on day 12 post-inoculation following active sensitization failed to prevent animals (7 of 8) from developing EAE compared to those (8 of 8) injected with L2 3D9, a control non-neutralizing hamster IgG1 monoclonal antibody reactive with mouse interleukin-2 (supplied by Dr. R. Schreiber in conjunction with Celltech, Slough, UK). However, there were reduced clinical manifestations (FIG. 5).

Figure 3:
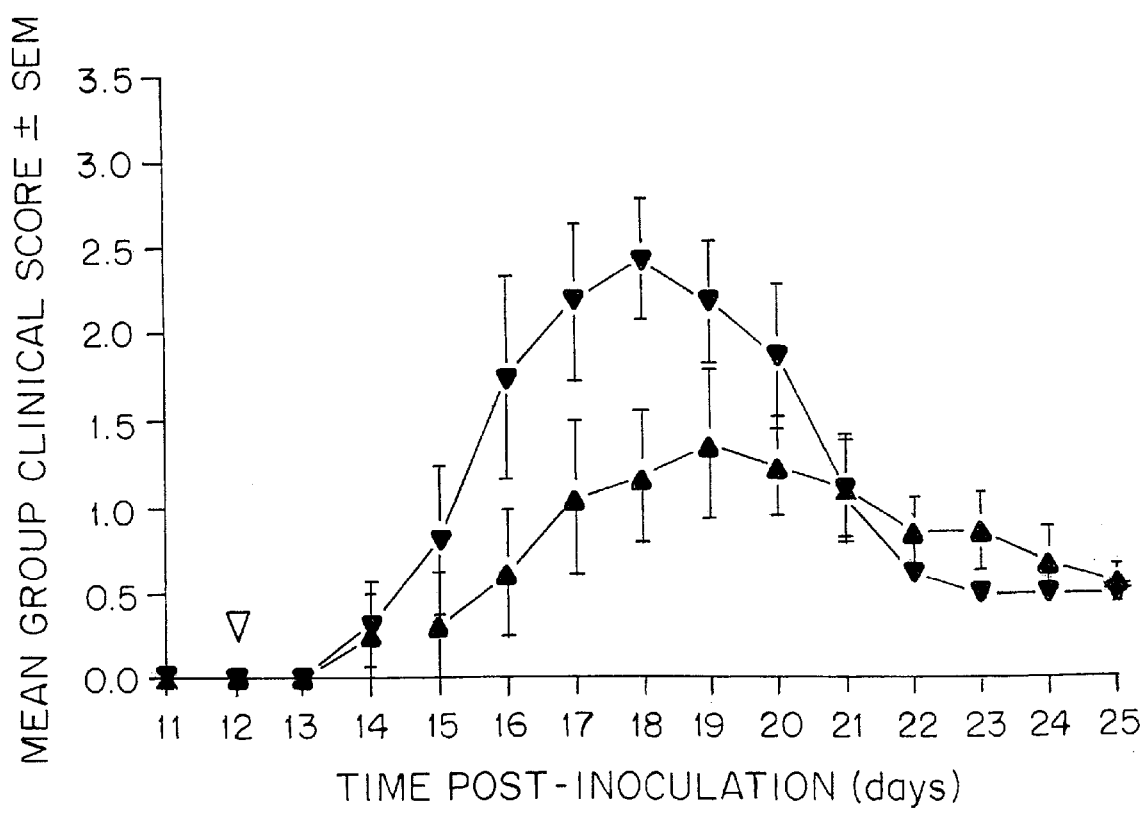
FIG. 3 is a graph illustrating the effect on EAE of a single injection of TNF-specific monoclonal antibody.

FIG. 3 illustrates the effect on EAE, specifically the effect on clinical signs, of a single injection of TNF-specific monoclonal antibody. The arrow indicates the day post-inoculation that the mice were injected intraperitoneally; the triangles represent the result from the mice that were injected intraperitoneally with 250 μg of TN3.19.12, a TNF-specific monoclonal antibody; and the inverse triangles represent the result from the mice that were injected intraperitoneally with 250 μg of L2 3D9, a control monoclonal antibody which is reactive with mouse interleukin-2. The results represent the mean clinical score of animals in each group ±SEM, at various times post-inoculation.

Although the data obtained failed to reach statistical significance, the results nevertheless indicate that mice injected with TN3.19.12 monoclonal antibody, compared with mice injected with L2 3D9 monoclonal antibody, appear to exhibit a delayed onset of weight loss (day 16.1±2.5 vs. 14.0±0.9) and clinical signs (day 17.0±2.0 vs. 15.4±1.2) and a lower severity of maximum clinical signs (2.1±1.1 vs. 3.1±0.9) and body weight loss (25.5±4.6% vs. 29.0±4.8%). Furthermore, although animals which developed clinical disease following TN3.19.12 monoclonal antibody treatment subsequently relapsed, with 6 of 7 animals relapsing (day of onset 38.3±7.5), control animals similarly relapsed, with 5 of 6 animals relapsing, on day 39.6±5.3 when observed to day 55 post-inoculation.

Thus, TN3.19.12 monoclonal antibody administered just prior to the onset of clinical manifestations can partially inhibit the onset of EAE by 2–3 days. Therefore animals were given multiple (250 μg) antibody doses, intraperitoneally at three-daily intervals (days 14, 17 and 20), initiated prior to and during the anticipated development of clinical disease (e.g., weight loss) (Table 1). In comparison to PBS and L2 3D9-treated controls, multiple doses of TNF-specific monoclonal antibody significantly inhibited the development of EAE when assessed up to 3 days following the cessation of treatment. In the few instances where animals were injected when weight loss was first detected, TN3.19.12-treatment appeared to stabilize weight loss. However, as shown in Table 1, although only 4 of 16 animals experienced clinical EAE during this period, within 10 days of monoclonal antibody treatment, the majority (13 of 16) of the animals subsequently developed clinical signs, although this represented a significant delay in the onset of clinical signs. Although not significantly different from PBS-injected animals, L2 3D9-treatment appeared to reduce the severity of clinical signs expressed (Table 1).

TABLE 1

Multiple Doses of Systemically Administered TNF-Specific mAb Inhibits the Development of EAE

| | Results up to Day 23 p.i. | | Results up to Day 30 p.i. | | |
| --- | --- | --- | --- | --- | --- |
| Treatment | No. EAE/Total | Clinical Score | No. EAE/Total | Clinical Score | Day of Onset |
| PBS | 13/15 | 2.6 ± 0.4 | 15/15 | 2.7 ± 0.4 | 17.7 ± 0.7 |
| Hamster Ig (L2 3D9) | 11/16 | 1.7 ± 0.4‡ | 14/16 | 1.8 ± 0.4 | 18.4 ± 1.4‡ |
| anti-TNF TN3.19.12 | 4/16* | 0.7 ± 0.3** | 13/16 | 1.1 ± 0.3* | 22.5 ± 0.7** |

*P < 0.01,
**P < 0.002 compared with the PBS treated group.
‡P < 0.05 compared with the TNF-i.p. treated group.

EXAMPLE 6

Systemic anti-TNF Immunotherapy after the Onset of Clinical Disease

SCH-immunized EAE animals were injected with TNF-specific monoclonal antibody when clinical signs were first manifested (day 0), that is when the animals were exhibiting a flaccid tail (grade 1). The mice were injected i.p. with 0.1 ml of either PBS, or 250 μg or 1 mg of TN3.19.12, a TNF-specific monoclonal antibody diluted in PBS, or 250 μg of L2 3D9, a hamster immunoglobulin monoclonal antibody diluted in PBS on days 0, 1 and 2 following the onset of clinical signs (FIGS. 4A–4B), or a single 250 μg injection i.p. of YTS 177.9, a CD4-specific monoclonal antibody diluted in PBS on day 0.

Figure 4A:
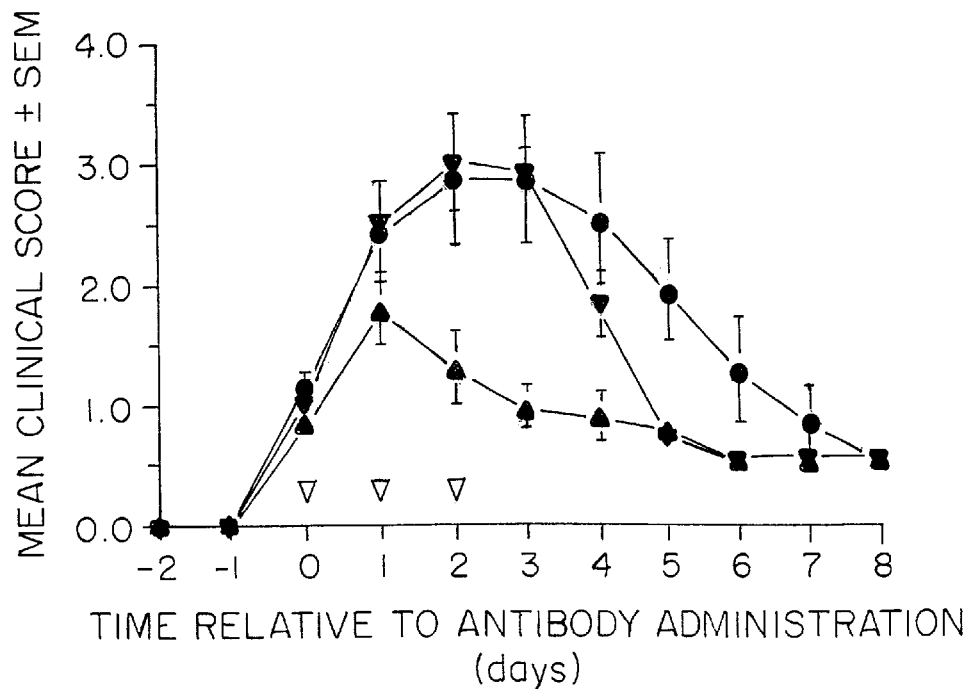
FIGS. 4A and 4B are a pair of graphs illustrating the inhibition of the development of clinical disease following the injection of TNF-specific monoclonal antibody.
Figure 4B:
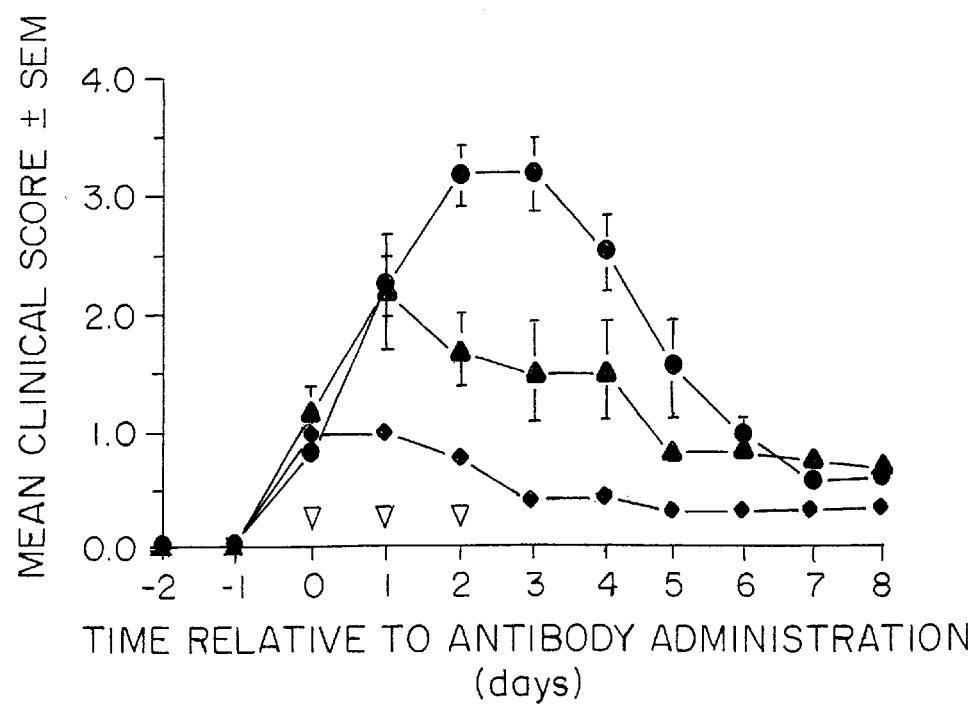

FIGS. 4A–4B shows the inhibition of the development of clinical disease following the injection of a TNF-specific monoclonal antibody. The arrows indicate days on which the mice were injected i.p.; the circles represent the results from the mice that were injected i.p. with 0.1 ml of PBS; the triangles represent the results from the mice that were injected i.p. with TNF-specific antibody; the inverse triangles represent results from the mice that were injected i.p. with 250 μg L2 3D9 monoclonal antibody; and the diamonds represent the results from the mice that were injected i.p. with 250 μg of YTS 177.9 monoclonal antibody on day 0.

FIG. 4A shows the results following injection i.p. of 250 μg of a TNF-specific antibody. FIG. 4B shows the results following injection i.p. of 1 mg of a TNF-specific antibody. The results represent the mean group clinical score ±SEM (n=5–7) following the onset of signs.

Following the first injection of TN3.19.12 monoclonal antibody the clinical signs progressed (FIGS. 4A–4B). Antibody treatment was therefore continued daily for a further 2 days. Within 2 days of the onset of the administration of 250 μg of TN3.19.12 monoclonal antibody, clinical signs abated and were significantly different from the clinical signs observed in L2 3D9-treated animals, whose disease became more severe. However, L2 3D9-treated animals appeared to remit at a faster rate than PBS-treated animals, indicating that this non-neutralizing IL-2-specific antibody may be exhibiting some biological inhibitory effect (FIG. 4A). Increasing the dose of TN3.19.12 monoclonal antibody administered to 1 mg failed to improve the inhibitory effect observed with administration of 250 μg TN3.19.12 monoclonal antibody (FIG. 4B), although this significantly diminished the severity of clinical disease compared with PBS-treated animals.

In contrast, a non-depleting CD4-specific monoclonal antibody could rapidly stabilize and reverse clinical progression (FIG. 4B). Although the mechanisms by which these antibodies act remain to be established, the observation that TNF-specific immunotherapy failed to inhibit an in vivo induced proliferative response whereas anti-CD4 treatment was markedly immunosuppressive (FIG. 5) indicated that these mechanisms are different.

EXAMPLE 7

Central Nervous System-directed TNF Immunotherapy

Following the onset of clinical signs, i.e., when the animals were exhibiting a flaccid tail (day 0), SCH-immunized EAE mice were injected intracerebrally (i.c.) in the cortex of the right frontal lobe as previously described (O'Neill, J. K., et al., *J. Neuroimmunol.* 35:53 (1992)) with varying doses of TN3.19.12 monoclonal antibody (FIG. 6): 150 μg, 15 μg, 1.5 μg, and 0 μg. Although 1.5 μg of TN3.19.12 monoclonal antibody failed to alter the clinical course of disease, 150 μg of monoclonal antibody stabilized clinical disease (FIG. 6).

Figure 6:
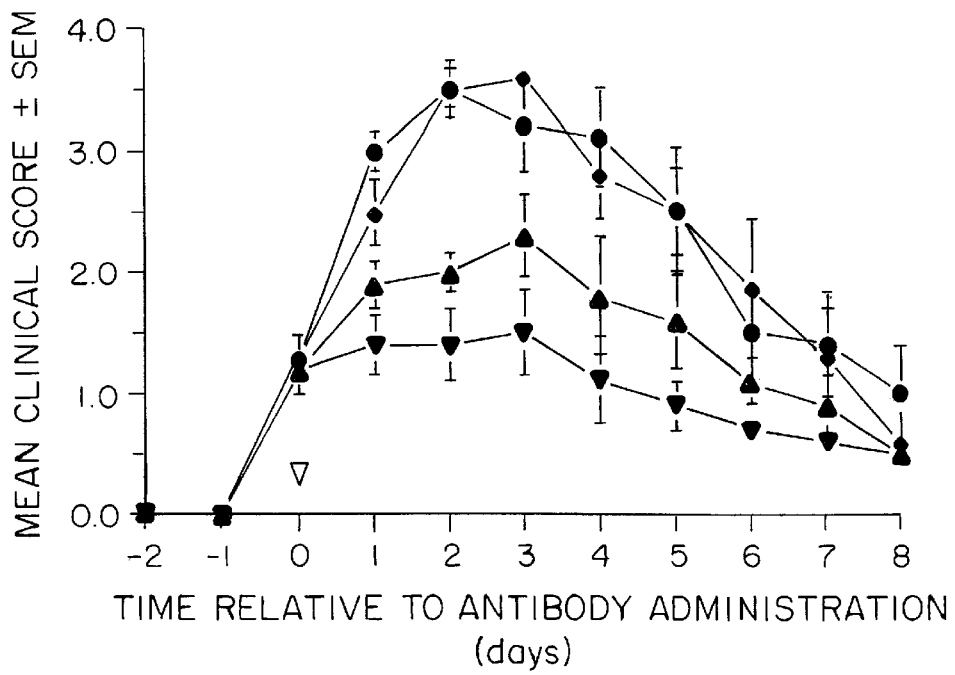
FIG. 6 is a graph illustrating the dose-dependent inhibition of the progression of clinical EAE following injection of TNF-specific monoclonal antibody directly into the central nervous system.

FIG. 6 thus shows the dose-dependent inhibition of the progression of clinical EAE following injection of TNF-specific monoclonal antibody directly into the central nervous system. The arrow indicates the onset of clinical signs when the animals were exhibiting a flaccid tail (day 0); the circles represent the results from the mice that were injected intracerebrally with 30 μl of PBS; the inverse triangles represent results from the mice that were injected intracerebrally with 150 μg TN3.19.12 monoclonal antibody; the triangles represent results from the mice which were injected intracerebrally with 15 μg TN3.19.12 monoclonal antibody; and the diamonds represent results from the mice that were injected intracerebrally with 1.5 μg of TNF-specific TN3.19.12 monoclonal antibody. The results represent the mean group score±SEM of 5 animals per group.

Figure 7:
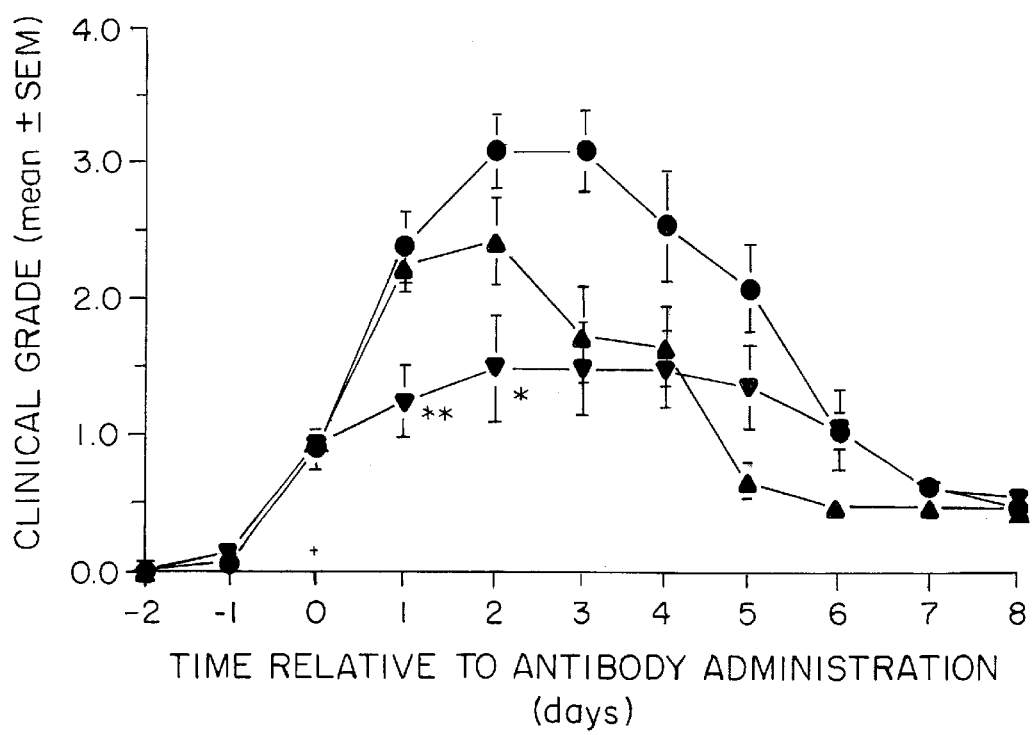
FIG. 7 is a graph illustrating the inhibition of the development of clinical disease following injection of TNF-specific monoclonal antibody directly into the central nervous system.

In additional experiments, following the onset of clinical signs, that is, when the animals were exhibiting a flaccid tail (day 0), SCH-immunized EAE mice were either untreated, or injected with 30 μl of PBS i.c. and 150 μg of TN3.19.12 monoclonal antibody i.p., or injected with 150 μg of TN3.19.12 monoclonal antibody i.c. and 30 μl of PBS i.p. (FIG. 7). Intracerebral injection was in the cortex of the right frontal lobe as previously described (O'Neill, J. K., et al., *J. Neuroimmunol.* 35:53 (1992)).

FIG. 7 illustrates the inhibition of the development of more marked clinical disease following injection of TNF-specific monoclonal antibody directly into the central nervous system. The arrow indicates the treatment at onset of clinical signs when the animals were exhibiting a flaccid tail (day 0); the circles represent results from mice that were untreated; the triangles represent results from mice injected with 30 μl of PBS i.c. and 150 μg of TNF-specific monoclonal antibody i.p.; and the inverse triangles represent results from mice injected with 150 μg of TNF-specific monoclonal antibody i.c. and 30 μl of PBS i.p. (FIG. 7). The mean clinical group score of 5–7 animals per group following the onset of clinical signs is shown.

The systemic i.p. injection of clinically-affected animals with 150 μg of monoclonal antibody TN3.19.12 again initially failed to rapidly prevent the progression of disease (FIG. 7). However, significant (double asterisk=$P<0.002$; single asterisk=$P<0.05$) benefit was observed when TNF immunotherapy (150 μg monoclonal antibody) was administered directly into the central nervous system (FIG. 7) compared to that administered systemically.

Figure 8A:
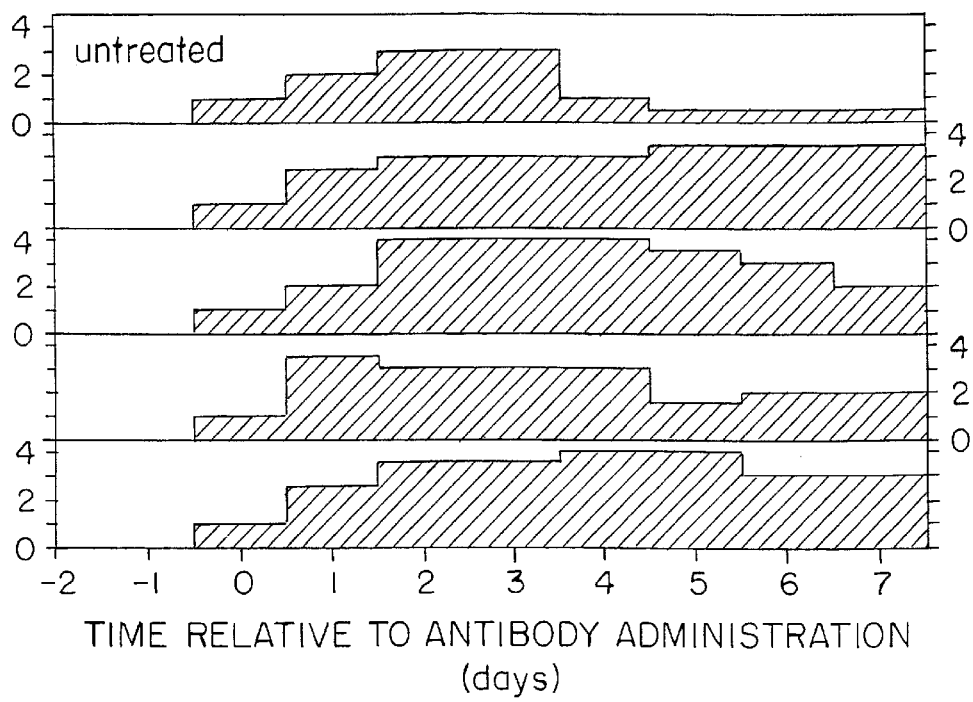
FIGS. 8A–8C are a set of three histograms illustrating the individual clinical grades of 5 different animals (in each group) following injection of TNF-specific monoclonal antibody directly into the central nervous system and intraperitoneally.
Figure 8B:
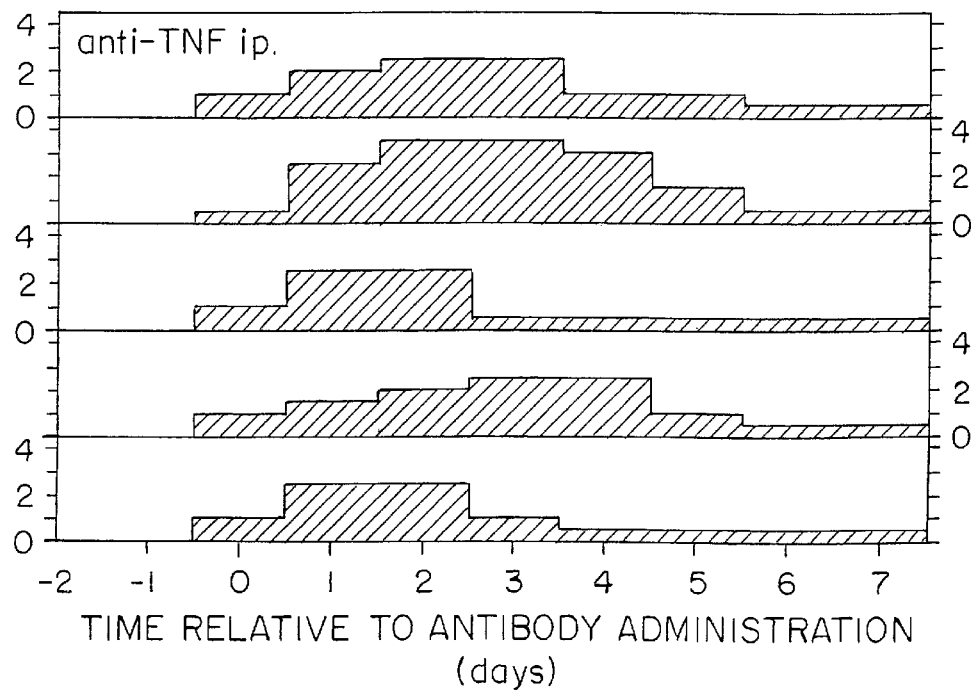
Figure 8C:
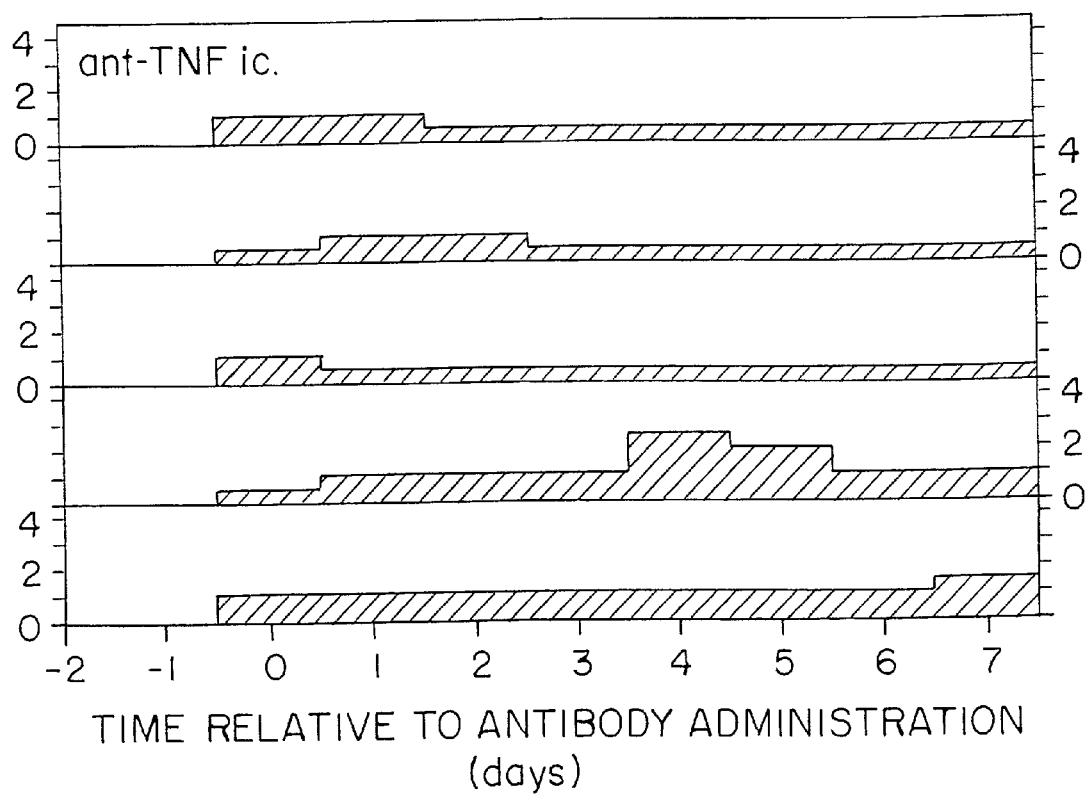

In contrast to the controls and to animals treated systemically with TN3.19.12 monoclonal antibody, where clinical signs always became more severe following disease onset, central nervous system-directed treatment generally stabilized clinical disease prior to remission, although in some cases animals experienced a transient increase in severity of signs following a period of stabilization (FIGS. 8A–8C).

In another experiment, following the onset of clinical signs, SCH-immunized EAE mice were treated as follows: untreated; injected intraperitoneally with 250 μg of YTS.177.9, a CD4-specific monoclonal antibody; injected intraperitoneally with 150 μg TN3.19.12, a TNF-specific monoclonal antibody, and intracerebrally with 30 μl of PBS; or injected intraperitoneally with 30 μl of PBS and intracerebrally with 150 μg of TN3.19.12 monoclonal antibody. As shown in Table 2, the results of this experiment indicate that intracerebral injection of TN3.19.12 monoclonal antibody significantly inhibited the progression of weight loss compared to both untreated animals and mice injected intraperitoneally with the TNF-specific antibody. In addition, although the majority of anti-TNF i.c.-treated animals (5 of 6) subsequently relapsed on day 35.6±5.3 and the majority of the control animals (5 of 6) also relapsed on day 38.4±3.4, the results indicate that this treatment modulates the severity of clinical disease. The data thus indicate that although CD4+ cells can be targeted in the peripheral circulation prior to extravasation into the central nervous system, TNF-pathogenesis/activity/secretion occurs mainly in the central nervous system, and that appropriately administered TNF-specific immunotherapy into the central nervous system can inhibit the progression of neuroimmunological disease.

immunized EAE mice were injected i.p. with varying doses of soluble human p55 sTNF-R (FIG. 10): 150 μg, 15 μg and 0 μg.

Figure 10:
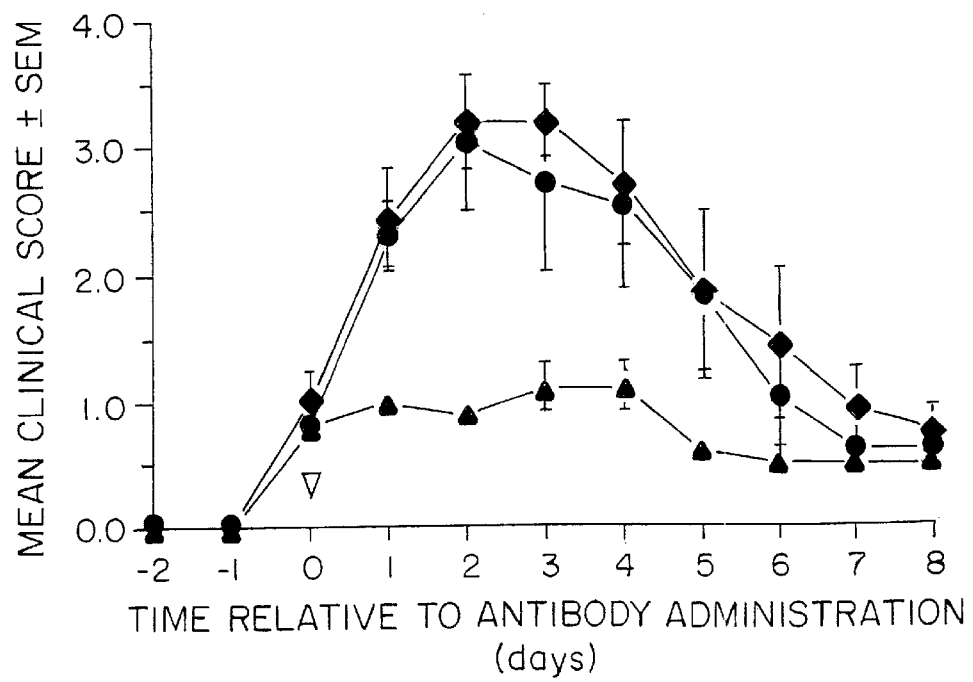
FIG. 10 is a graph illustrating the inhibition of EAE by systemic injection of a soluble human p55-TNF receptor.

FIG. 10 shows the dose-dependent inhibition of the progression of clinical EAE following the injection of soluble human p55 sTNF-R. The arrow indicates the treatment at onset of clinical signs when the animals were exhibiting a flaccid tail (day 0); the circles represent the results from the mice that were injected i.p. with 30 μl of PBS; the diamonds represent the results from the mice that were injected i.p. with 15 μg of SF2 TNF-R; and the triangles represent the results from the mice that were injected i.p. with 150 μg of SF2 TNF-R. The results represent the mean clinical score ±SEM of 5–6 animals per group. The results show that the systemic effect of soluble human p55 TNF receptor is at 15–150 μg/injection, and thus is more effective than the systemic effect of the TNF monoclonal antibody TN3.19.12.

TABLE 2

Direct Administration of Anti-TNF Antibody Into the CNS Inhibits Progressive Weight Loss During Clinical EAE Episodes

| Treatment i.p. | none | anti-CD4 | anti-TNF | PBS |
|---|---|---|---|---|
| Treatment i.c. | none | none | PBS | anti-TNF |
| Number Analyzed | 20 | 10 | 12 | 13 |
| Mean Weight at onset of treatment (g) | 18.1 ± 1.3 | 18.1 ± 1.6 | 18.5 ± 2.5 | 18.1 ± 2.9 |
| Mean Relative Weight Change 24 hours after treatment (g) | −1.37 ± 0.11 | +0.82 ± 0.20* | −1.00 ± 0.18* | −0.08 ± 0.21*,‡ |

*P < 0.002 compared to untreated group.
‡P <0.002 i.p. anti-TNF group compared with i.c. anti-TNF treatment group.

EXAMPLE 8

Central Nervous System-directed Tumour Necrosis Factor Receptor Immunotherapy

Figure 9:
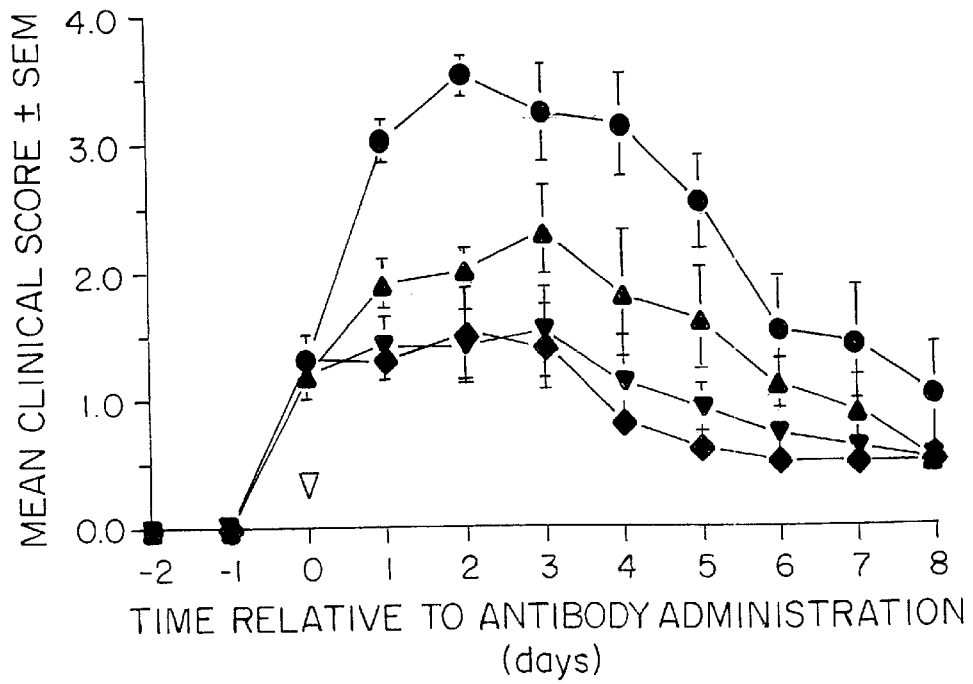
FIG. 9 is a graph illustrating the greater inhibition of EAE by intracerebral injection of a TNF-specific monoclonal antibody or of a soluble human p55-TNF receptor, than by intraperitoneal injection.

Following the onset of clinical signs, that is when the animals were exhibiting a flaccid tail (day 0), SCH-immunized EAE mice were injected i.c. with 15 μg of soluble human p55 SF2, a TNF receptor, or varying doses (0 μg, 15 μg, or 150 μg) of TN3.19.12, a TNF-specific monoclonal antibody (FIG. 9).

FIG. 9 shows the inhibition of the development of clinical disease following the injection of a TNF-specific monoclonal antibody and following the injection of a soluble human p55 TNF receptor. The arrow indicates the treatment at onset of clinical signs when the animals were exhibiting a flaccid tail (day 0); the circles represent the results from the mice that were injected i.c. with 30 μl of PBS; the triangles represent the results from the mice that were injected i.c. with 15 μg of TNF-specific monoclonal antibody; the inverse triangles represent the results from the mice that were injected i.c. with 150 μg of TNF-specific monoclonal antibody; and the diamonds represent the results from the mice that were injected i.c. with 15 μg of soluble human p55 TNF-R. The results represent the mean clinical score ±SEM of 5–6 animals per group. The results observed when injecting i.c. with 15 μg of soluble human p55 SF2 TNF-R is similar to the results observed when injecting i.c. with 150 μg of anti-TNF monoclonal antibody, indicating, in this instance, the greater potency of the SF2 TNF-R.

EXAMPLE 9

Systemic Tumour Necrosis Factor Receptor Immunotherapy

Following the onset of clinical signs, i.e., when the animals were exhibiting a flaccid tail (day 0), SCH- Equivalents Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method of treating multiple sclerosis in a mammal, comprising administering to said mammal a therapeutically effective amount of a monoclonal anti-tumor necrosis factor alpha antibody which ameliorates the effects of multiple sclerosis, wherein said antibody is administered after onset of the multiple sclerosis.

2. A method of claim 1 wherein the mammal is a human being.

3. A method of claim 2 wherein the anti-tumor necrosis factor alpha antibody is administered in a pharmaceutically-acceptable vehicle.

4. A method of claim 2 wherein a therapeutically effective amount of an anti-tumor necrosis factor alpha antibody is administered directly to the central nervous system of the human being.

5. A method of claim 4 wherein the anti-tumor necrosis factor alpha antibody is administered intrathecally.

6. A method of claim 2 wherein the anti-tumor necrosis factor alpha antibody is an antigen binding antibody fragment.

7. A method of treating multiple sclerosis in a mammal, comprising administering to said mammal a therapeutically effective amount of a soluble tumor necrosis factor alpha receptor which ameliorates the effects of multiple sclerosis, wherein said receptor is administered after onset of the multiple sclerosis.

8. A method of claim 7 wherein the mammal is a human being.

9. A method of claim 8 wherein the soluble tumor necrosis factor alpha receptor is administered in a pharmaceutically-acceptable vehicle.

10. A method of claim 8 wherein a therapeutically effective amount of a soluble tumor necrosis factor alpha receptor is administered directly to the central nervous system.

11. A method of claim 8 wherein the soluble tumor necrosis factor alpha receptor is administered intrathecally.

12. A method of claim 8 wherein the soluble tumor necrosis factor alpha receptor is a binding fragment thereof.

13. A method of claim 8 wherein the soluble tumor necrosis factor alpha receptor is a soluble human p55-tumor necrosis factor alpha receptor.

14. A method of claim 13 wherein the soluble human p55-tumor necrosis factor alpha receptor is a binding fragment thereof.

15. A method of treating multiple sclerosis in a human being, comprising administering directly to the central nervous system of said human being a therapeutically effective amount of an anti-tumor necrosis factor alpha antibody, wherein said antibody is administered after onset of the multiple sclerosis.

* * * * *